United States Patent
Myllenbeck et al.

(10) Patent No.: US 12,077,719 B2
(45) Date of Patent: Sep. 3, 2024

(54) ALKYL DIALKOXYALKANOATES AS BIODERIVED, HIGH CETANE DIESEL FUELS

(71) Applicant: National Technology & Engineering Solutions of Sandia, LLC, Albuquerque, NM (US)

(72) Inventors: Nicholas Myllenbeck, Livermore, CA (US); Ryan Wesley Davis, San Jose, CA (US); Eric Monroe, Melrose, MA (US); Joseph Carlson, Castro Valley, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 17/958,560

(22) Filed: Oct. 3, 2022

(65) Prior Publication Data

US 2023/0097524 A1    Mar. 30, 2023

Related U.S. Application Data

(62) Division of application No. 17/473,669, filed on Sep. 13, 2021, now Pat. No. 11,492,565.

(51) Int. Cl.
| | |
|---|---|
| *C10L 1/19* | (2006.01) |
| *C07C 67/08* | (2006.01) |
| *C10L 10/12* | (2006.01) |

(52) U.S. Cl.
CPC ............... *C10L 1/19* (2013.01); *C07C 67/08* (2013.01); *C10L 10/12* (2013.01);
(Continued)

(58) Field of Classification Search
CPC ....... C07C 67/08; C07C 69/67; C10L 1/1852; C10L 1/19; C10L 10/12;
(Continued)

(56) References Cited

U.S. PATENT DOCUMENTS

2010/0292491 A1* 11/2010 Selifonov ............ C07D 407/12
549/454
2020/0369951 A1* 11/2020 Quraishi .................. C09K 8/74

FOREIGN PATENT DOCUMENTS

EP            2738154 A1       6/2014

OTHER PUBLICATIONS

Gaspar, et al., "Top 13 Blendstocks Derived From Biomass for Mixing-Controlled Compression-Ignition (Diesel) Engines", in Co-Optimization of Fuels & Engines, U.S. Department of Energy Office of Energy Efficiency & Renewable Energy, 145 pages.

(Continued)

*Primary Examiner* — Latosha Hines
(74) *Attorney, Agent, or Firm* — Eschweiler & Potashnik, LLC; Samantha Updegraff

(57) ABSTRACT

A fuel for an internal combustion engine includes a $C_5$ to $C_{30}$ dialkoxyalkanoate corresponding to formula (I):

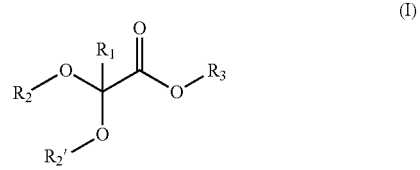

wherein the $R_1$ group is —H or a —$CH_3$ group, the $R_2$ and $R_2'$ groups are alkyl groups independently selected to have 1 to 9 carbon atoms; and the $R_3$ group is selected to have 1
(Continued)

to 9 carbon atoms. The compounds described herein may be used as neat fuels or mixed fuels (with diesel, biodiesel, jet fuel, marine fuel or other fuel compounds) in autoignition or spark ignition engines, such as diesel engines, gasoline (spark ignition) engines, MCCI, Homogeneous Charge Compression Ignition (HCCI) engines, or more generally in Low-Temperature Gasoline Combustion (LTGC) engines (using gasoline-like fuels), that have the high-efficiency advantages of HCCI but can operate with some level of charge inhomogeneities. Methods of making these compounds are environmentally friendly and can be done in a continuous manner.

18 Claims, 4 Drawing Sheets

(52) U.S. Cl.
CPC ............... *C10L 2200/0423* (2013.01); *C10L 2200/0446* (2013.01); *C10L 2270/02* (2013.01)

(58) Field of Classification Search
CPC ..... C10L 2200/0423; C10L 2200/0446; C10L 2200/0476; C10L 2270/02; C10L 2270/026
See application file for complete search history.

(56) References Cited

OTHER PUBLICATIONS

Huq, et al., "Performance-Advantaged Ether Diesel Bioblendstock Production by a Priori Design", in PNAS, vol. 116, No. 52, Dec. 26, 2019, pp. 26421-26430.
Pereira, et al., "Green Fuel Production Using the PermSMBR Technology", in Industrial & Engineering Chemistry Research, American Chemical Society, vol. 51, 2012, pp. 8928-8938.
Tietze, L. F. et al., "Synthesis of Alkyl Propanoates by a Haloform Reaction of a Tricholoro Ketone: Ethyl 3,3-Diethoxypropanoate," Organic Synthesis, Coll. vol 8, p. 254 (1993); vol. 69, p. 238 (1990).
Zhang, Z. et al., "Catalytic Conversion of Bio-Oil to Oxygen-Containing Fuels by Acid-Catalyzed Reaction with Olefins and Alcohols over Silica Sulfuric Acid," Energies (2013) 6:4531-4550.

* cited by examiner

| Example No. | $R_1/R_2/R_3$ | Isolated yield (g, %), [98+ % purity] | Normal boiling point (°C, DSC) | Fuel Properties | Cloud point |
|---|---|---|---|---|---|
| 2 | Me/isopentyl/isopentyl | 131 g, 75 % | 255 | DCN=53.1, LHV=32.4, YSI/kg=337<br><br>DCN=51.4, LHV=38.2 (flow chemistry) | <-60°C |
| 3 | Me/isobutyl/isobutyl | 168 g, 79 % | 231 | DCN=38.6, LHV=28.52, YSI/kg=319 | <-60°C* |
| 4 | Me/n-butyl/n-butyl | 115 g, 69 % | 252 | DCN=60.0, LHV=28.41, YSI/kg=256 | <-60°C* |
| 5 | Me/isoamyl/ethyl (DAOA') | 83 g, 75 % (reaction b) | 241 | DCN=48.0, LHV=28.53, YSI/kg=298 | |
| 6 | Me/ethyl/isoamyl (DAOA') | 56 g, 51 % (reaction b) | 228 | DCN<33, LHV=31.03 | |
| 7 | H/isoamyl/isoamyl | 156 g, 95 % | 280 | DCN 63.3, LHV=34.43 | <-60°C* |
| 8 | Me/ethyl/ethyl | 74 g, 44 % | 170 | DCN<33, LHV=27.3 | <-60°C |
| Control | Acetaldehyde diisoamyl acetal (control) | 77 g, 84 % | 150-200* | DCN>64, LHV=38.3 | <-60°C |

*Fig. 2*

| Fuel Candidate | Chemical Structure | Derived Cetane Number | Lower Heating Value (MJ/kg) | Yield Sooting Index (YSI/kg) | Cloud Point (°C) |
|---|---|---|---|---|---|
| Soy biodiesel | Mixture of saturated, mono-, di-, tri-unsaturated $C_{14}$-$C_{22}$ fatty acid methyl esters | 52 | 37 | 434 | 0.5 |
| Isopentyl 2-(isopentyloxy) propanoate | 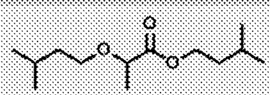 | 42.6 | 34.5 | 372 | <-50 |

ALKYL DIALKOXYALKANOATES AS BIODERIVED, HIGH CETANE DIESEL FUELS

RELATED APPLICATIONS

This application is a divisional of prior application Ser. No. 17/473,669, filed Sep. 13, 2021, titled Alkyl Dialkoxyalkanoates as Bioderived, High Cetane Diesel Fuels, the entirety of which is incorporated herein by reference.

STATEMENT OF GOVERNMENTAL INTEREST

This invention was made with Government support under Contract No. DE-NA0003525 awarded by the United States Department of Energy/National Nuclear Security Administration. The Government has certain rights in the invention.

FIELD

This disclosure relates to biomass conversion into fuel and fuel blending agents. More specifically, this disclosure relates to diesel fuel and fuel blending agents for internal combustion engines.

BACKGROUND

Combustion of liquid fossil fuels for transportation is a major source of carbon emissions. Biodiesels are increasingly used to supplement conventional petroleum-derived fuels for transportation. As a renewable energy source, biodiesels help to reduce dependence on fossil-fuel, mitigate greenhouse-gases emissions, and in some cases, improve air quality. New renewable transportation fuels derived from abundant sources of biomass will be needed to further offset fossil fuel use. Mandates for biodiesels have been established around the world, requiring an even larger increase in biodiesel usage in the future. For example, to support the growing desire to reduce greenhouse gas emissions and establish energy independence, the United States is mandated by federal law to produce 1 billion gallons a year of renewable transportation fuel.

Biodiesel is defined as "a fuel comprised of monoalkyl esters of long-chain fatty acids derived from vegetable oils or animal fats, designated B100." Standard Specification for Biodiesel Fuel Blend Stock (B100) for Middle Distillate Fuels. In ASTM D6751-19, 2019. Biodiesel is typically produced using methanol by conversion of triglycerides into fatty acid methyl esters (FAMEs), where the fatty acid profile of the lipid source used will determine the fuel properties. While biodiesel has successfully penetrated the fuel market, with production reaching 2.2 billion gallons in 2016, poor performance in important fuel properties such as cold flow continue to limit the application of large blend volumes in cold weather environments. See Shrestha, D.; Van Gerpen, J.; Thompson, J.; Zawadzki, A. in Cold flow properties of biodiesel and effect of commercial additives, 2005 ASAE Annual Meeting, 2005; American Society of Agricultural and Biological Engineers: 2005; p 1; Monirul, I.; Masjuki, H.; Kalam, M.; Zulkifli, N.; Rashedul, H.; Rashed, M.; Imdadul, H.; Mosarof, M., A comprehensive review on biodiesel cold flow properties and oxidation stability along with their improvement processes, RSC advances 2015, 5, (105), 86631-86655; and Bolonio, D.; Llamas, A.; Rodriguez-Fernández, J.; Al-Lal, A. M.; Canoira, L.; Lapuerta, M.; Gómez, L., Estimation of cold flow performance and oxidation stability of fatty acid ethyl esters from lipids obtained from *Escherichia coli*. Energy & Fuels 2015, 29, (4), 2493-2502. Cold temperatures cause typical biodiesel fuels to gel and clog fuel filters. Today's highest-volume commercial MCCI (mixing-controlled compression ignition) biodiesel, lipid-based biodiesel, typically exhibits poor cold-weather performance that limits its use in much of the world. Yet bioderived intermediates and fermentation products are typically unsuitable for use in MCCI engines or cannot be produced at high rates, yields, and titers. To address these challenges, efforts have been made to discover new bioderived fuels for diesel engines that have improved fuel properties.

In addition, to discovering effective, new, and renewable bioderived fuels, it is desirable that the methods of making such are efficient and environmentally sound. This is not the case with all conversion processes, which may involve undesirable halogenated reactants, heavy metals or other contaminants.

SUMMARY

Disclosed herein is a chemical upgrading of high volume fermentation products to produce a novel biodiesel with properties desirable for use in mixing-controlled compression ignition (MCCI) engines. In particular, alkyl dialkoxyalkanoate biodiesels were synthesized by one-pot, triple condensation of primary aliphatic alcohols with pyruvic acid and glyoxylic acid, giving rise to symmetrical ester and ketal functionalities. A further base catalyzed step allowed for chemoselective interchanging of the ester group with no modification to the ketal/acetal groups. The synthesis and isolation of these compounds at high purity was demonstrated and the application of flow chemistry (continuous synthesis) was also demonstrated. In an embodiment, the process used is environmentally friendly and in accordance with the twelve principles of green chemistry as set forth by the U.S. Environmental Protection Agency (EPA).

The derived cetane number (DCN) of the pure compounds may be in the range of 40-63, depending on the identity of the alcohol and acid used (petro-diesel often is in the range of 42-45). These compounds show promise as a diesel alternative in autoignition (compression ignition) engines and may also have favorable properties for spark ignition engines. For autoignition engines, these properties include low cloud point, low sooting index, high energy content, and high cetane (DCN).

In addition to the promising fuel properties, the theoretical production yield for these molecules have the potential to be substantial and can incorporate low-quality biomass hydrolysates. The fusel alcohols and alpha-carbonyl containing acids are readily available by microbial fermentation; therefore, fuels derived from these feedstocks may permit broader use of renewable diesel fuels.

In an embodiment, a fuel for an internal combustion engine comprises a $C_5$ to $C_{30}$ dialkoxyalkanoate corresponding to formula (I):

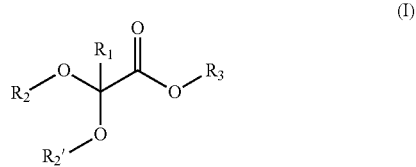

The $R_1$ group is —H or a —$CH_3$ group. The $R_2$ and $R_2'$ groups are independently selected from an alkyl group selected to have 1 to 9 carbon atoms; and the $R_3$ group is selected to have 1 to 9 carbon atoms. Typically, $R_2$ and $R_2'$ will be the same, unless a mixture of starting materials is used.

The compounds described herein may be used as neat fuels or mixed fuels (with diesel, biodiesel, marine fuel or other fuel compounds) in autoignition or spark ignition engines, such as diesel engines, gasoline (spark ignition) engines, MCCI, Homogeneous Charge Compression Ignition (HCCI) engines, or more generally in Low-Temperature Gasoline Combustion (LTGC) engines (using gasoline-like fuels), that have the high-efficiency advantages of HCCI but can operate with some level of charge inhomogeneities.

In an embodiment, a blended fuel for an internal combustion engine comprises the compound from Formula I above and a fuel selected from the group consisting of: gasoline, diesel, alcohol fuel, biodiesel, jet fuel, marine fuel, Fischer-Tropsch fuel, or combinations thereof.

In an embodiment, an enhanced fuel for an internal combustion engine includes the dialkoxyalkanoate of Formula I and a portion of a fuel selected from the group consisting of: diesel, gasoline, alcohol fuel, biodiesel, jet fuel, marine fuel, Fischer-Tropsch fuel, or combinations thereof; and a portion of an alkoxyalkanoate compound.

In an embodiment, a method for powering an internal combustion engine includes the steps of combusting a fuel to drive a piston in a cylinder of the engine. In an embodiment, a method for making a fuel product for an internal combustion engine at least partially from a biomass source, the method comprising: reacting a $C_1$ to $C_9$ alcohol and an alpha-carbonyl acid in a solvent to form a dialkoxyalkanoate, wherein the dialkoxyalkanoate is a $C_5$ to $C_{30}$ dialkoxyalkanoate. This step is acid catalyzed. This can be done as part of a continuous process. A base-catalyzed additional transesterification reaction can be done to react a different alcohol onto the compound. These steps can be performed with environmentally sound reactants and can be scaled up efficiently.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something and is not intended to indicate a preference.

In an embodiment, a fuel composition consists essentially of the dialkoxyalkanoate reaction product. "Consisting essentially of" in this instance, means the specified materials and those that do not materially affect the basic and novel characteristics of the methods, articles of manufacture, or compositions listed herein. For example, an unspecified material that does not materially affect the basic and novel characteristics of the methods, articles of manufacture, or compositions listed herein, in an amount of less than about 5%, less than about 3%, or less than about 1% may be encompassed by this term.

BRIEF DESCRIPTION OF THE DRAWINGS

FIG. 2 shows several compounds made and tested for various properties to determine the effect of structure of the properties of the compound.

DETAILED DESCRIPTION

Figure 1:
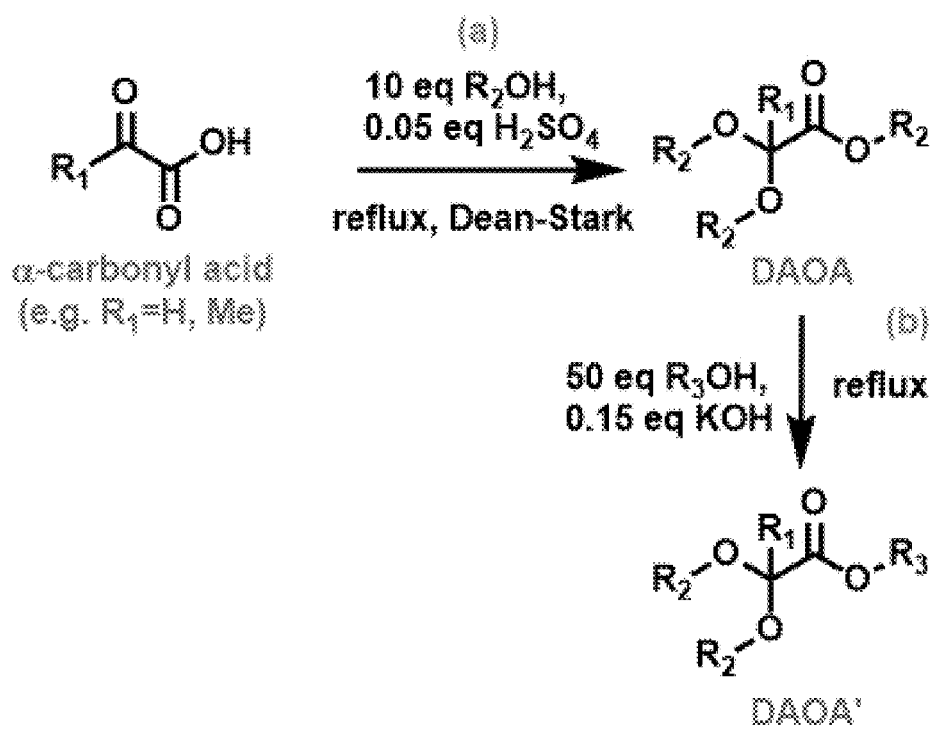
FIG. 1 shows an example overall reaction scheme.

Demonstrated herein is an environmentally friendly approach to address biodiesel insufficiencies, such as those mentioned above, by combining compounds readily available from biomass sources, that is: alpha carbonyl acids (such as pyruvic acid, glyoxylic acid) and alcohols (such as, e.g., fusel alcohols).

In an embodiment, alpha-carbonyl acids such as pyruvic acid can also be obtained from biomass, for example, via glycolysis of glucose. See Zhengshan Luo, et al, "Enhancement of pyruvic acid production in *Candida glabrata* by engineering hypoxia-inducible factor 1," Bioresource Technology, Vol. 295, 2020, 122248, ISSN 0960-8524. Various biomass intermediates can be converted into fusel alcohols at mass yields up to 60%, such as 40 to 55%, or 45 to 50%. Both products can also be produced rapidly, cheaply, and at high concentrations from a wide range of biomass feedstocks using established industrial processes.

However, neither alpha-carbonyl acids nor fusel alcohols alone have properties suitable for MCCI fuel.

Thus, the biomass alcohol and alpha-carbonyl acid were combined and upgraded via triple acid-catalyzed condensation, resulting in a $C_5$-$C_{30}$ dialkoxyalkanoate.

Testing of this and other compounds revealed desirable properties for MCCI. A cloud point (the temperature at which liquid begins to solidify) of less than −60° C. also suits it for cold-weather operation—a major advantage over traditional biodiesel. It is believed that these improvements are due to increased chemical branching and increased oxygen content.

The combined biological and chemical synthesis pathway converts cellulosic biomass at significant and substantial overall mass yields. Accordingly, the presently described process and product provides for a substantial improvement in the use of renewable biomass products for fuels.

An advantage of biodiesels are the renewable resources, such as biomass, available as starting materials. Sources of biomass include dedicated energy crops, such as herbaceous or woody crops; crop residues, such as stalks and leaves of agricultural crops; forestry residues, such as unmerchantable timber remnants; and even algal or cyanobacterial feedstocks. Other sources include wood processing residues, such as sawdust; municipal waste, such as sorted recyclable materials; or wet waste, such as food waste and sewage. The biomass source should be amenable to solubilization and hydrolysis of biopolymers contained therein.

In general, the biomass should be pretreated to solubilize and hydrolyze the biopolymers (e.g., cellulose or proteins). This can be done by dilute acid hydrolysis. The hydrolysate should be pH adjusted from about 0 to about 5.2 for fermentation, such as 2 to 5, or 3 to 4.5.

Conversion of raw biomass to the starting material of the novel process disclosed can be accomplished by conversion of hydrolysates in the biomass using biological catalysts (including, e.g., *Saccharomyces, E. coli, Lactobacillus,*

*Clostridium*, and a host of others). This generates a variety of common high-yielding intermediates from various acidogenic and solvetogenic biochemical pathways in homo- or heterofermentative processes. See Chapter 11: Fermentation Pathways, Microbial Physiology. Albert G. Moat, John W. Foster and Michael P. Spector (2002). ISBN: 0-471-39483-1, incorporated herein by reference. Furthermore, recent advances in synthetic biology and metabolic engineering significantly expand the ability to generate a host of biochemical intermediates with substantially improved bioconversion rates, yields, and titers. See Choi, et al, "Systems Metabolic Engineering Strategies: Integrating Systems and Synthetic Biology with Metabolic Engineering," Trends in Biol. Vol. 37, 8, p. 817-837, Aug. 1, 2019, incorporated herein by reference.

Among the biochemical compounds within 1-2 enzymatic steps from central metabolism are a variety of short-chain ($C_2$-$C_5$) alcohols, including ethanol, (iso)propanol, (iso)butanol, and (iso)pentanols, commonly denoted as 'fusel' alcohols. See Noor, et al, "Central Carbon Metabolism as a Minimal Biochemical Walk between Precursors for Biomass and Energy," Molecular Cell Vol. 39 Iss. 5, p. 809-820 (Sep. 10, 2010), incorporated herein by reference. For pyruvic acid, glycolysis is the pathway for conversion. For glyoxylic acid ($R_1$=H), that is derived biologically from glycolic acid oxidation or during the glyoxylate cycle from isocitrate. In turn, glycolic acid can be accessed through ethylene glycol.

In an embodiment, to valorize the biomass intermediates, chemical coupling of the alpha carbonyl acids and fusel alcohols retrieved from biomass was performed. The coupling was performed at the carboxylic acid and carbonyl reactive sites to generate a suite of tri-functional conjugates exhibiting two ether and one ester moiety, with stoichiometries of 1 dialkoxyalkanoate: 3 alcohols. The process makes use of environmentally friendly reagents, and in an embodiment, alkyl halides are not used or generated.

An example overall reaction scheme is shown in FIG. 1. Step (a) of FIG. 1 shows the alpha-carbonyl acid component with the alcohol component being added, along with an acid catalyst.

In an embodiment, the acid may be selected from strong acids, for example, acids that are environmentally friendly, such as sulfuric acid, nitric acid, or a solid-supported strong acid, such as Amberlyst-15 (a macro reticular polystyrene based ion exchange resin with strongly acidic sulfonic group).

In an embodiment, the alcohol is a fusel alcohol ($C_2$ to $C_5$) as discussed above. In another embodiment, the alcohol is a $C_6$ to $C_{18}$ alcohol, such as $C_8$ to $C_{16}$, or $C_{10}$ to $C_{14}$ alcohol. The alcohol can be linear or branched, and may comprise a cyclic and/or aryl group. The alcohol may be primary, secondary, or tertiary. In an embodiment, the alcohol can be a mixture of different alcohols to obtain different $R_2$ and $R_2'$ groups in some of the products.

In an embodiment, the alpha-carbonyl acid is selected from pyruvic acid or glyoxylic acid.

In an embodiment, the reaction is run in bulk, e.g., with the fusel alcohols forming the solvents, but non-polar solvents such as hexane or toluene may be used as co-solvents to facilitate azeotroping.

The reaction mixture is refluxed with a Dean Stark separator for several hours, such as 1 to 24 hours, e.g., 6 to 18 hours, or until substantial completion of the reaction. This produces a dialkoxyalkanoate with three functional groups having the R group as in the starting alcohol component. This is an equilibrium-driven reaction that depends on water removal efficiency. Water is removed via the Dean-Stark apparatus by azeotropic layer separation.

The dialkoxyalkanoate reaction mixture can be directly washed with water, $NaHCO_3$ and saturated salt (NaCl) solution. A non-polar organic solvent such as hexane or diethyl ether can be used to facilitate layer separation. The organic layer can be dried (such as by using anhydrous $MgSO_4$), filtered, and concentrated in vacuo. The product can be purified by methods such as flash chromatography and distillation.

In a second step, shown in FIG. 1 as step (b), a base-catalyzed transesterification reaction is performed which allows desymmetrization of $R_2$/$R_3$ groups. In other words, the $R_2$ group of the ester is replaced, allowing the compound to having non-symmetric functionalities. This is accomplished by a similar reflux reaction as step (a), but that is catalyzed with a base, such as KOH. In an embodiment of step (b), the product from reaction step (a) can be added, such as in a metered manner over several minutes, e.g., 5 to 30 minutes, or 10 to 20 minutes, and stirred. Then, the desired base can be added and the reaction mixture can be brought to reflux for several hours, such as 1 to 24 hours, e.g., 6 to 18 hours, or until substantial completion to produce the dialkoxyalkanoate.

The dialkoxyalkanoate reaction mixture can be directly washed with water, $NaHCO_3$ and saturated salt (NaCl) solution. A non-polar organic solvent such as hexane or diethyl ether can be used to facilitate layer separation. The organic layer can be dried (such as by using anhydrous $MgSO_4$), filtered, and concentrated in vacuo. The product can be purified by methods such as flash chromatography and distillation. Through the reactions, the carbonyl group and the acid group of the alpha-carbonyl acid react to couple to the alcohol groups.

This procedure can be used to react blends of alcohols and blends of alpha-carbonyl acids to produce blended products of dialkoxyalkanoates.

In an embodiment, the reaction can be run in a continuous manner. In this embodiment, a batch reaction according to step (a) is run until sufficient conversion, e.g., 90% or more, such as 95% or more is achieved. This batch reaction is utilized to provide a pool of substantially fully reacted material to begin pumping out in stage 2. This batch reaction may take 2-8 hours, e.g., 3 to 6 hours.

Next in a continuous reaction step, a pump is used to pump out the reaction product, and then or simultaneously, the pumped out material is replaced with fresh, unreacted reagents (premixed alpha-carbonyl acid, alcohol, and acid catalyst stored at room temperature). The addition of new reactants can be done at the same rate as the extraction of reaction product (thus achieving steady-state reactor volume). The inflow rate should be effectively set so that the residence time ($t_{res}$=$V_{reactor}$/flow rate) is sufficient to convert most of the newly pumped-in unreacted reagents to product. This stage can go on indefinitely, e.g., for 2 to 10 days, or 1 to 10 months, or even years, so long as a properly matched inflow and outflow of reagents is maintained. The same reaction conditions are used in this step as the other steps.

Once the desired amount of product has been made or fresh reagents are fully used up, the pumping in/out of the system is halted, and the reagents in the reaction vessel are allowed to react for an additional 2-8 hours to maximize conversion. Then, the reaction mixture is poured out and combined with the effluent from the other phases and purified as discussed above for this class of compounds.

The term dialkoxyalkanoate is meant to encompass the reaction product of the process described herein where an alpha-carbonyl acid and an alcohol are the starting materials, and a strong acid catalyst, such as sulfuric acid or Amberlyst-15 is also used.

The dialkoxyalkanoate is a $C_5$ to $C_{30}$ compound corresponding to formula (I):

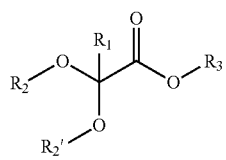

(I)

The $R_1$ group is —H or a —$CH_3$ group. The $R_2$ and $R_2'$ groups are independently selected from an alkyl group selected to have 1 to 9 carbon atoms; and the $R_3$ group is selected to have 1 to 9 carbon atoms. Typically, $R_2$ and $R_2'$ will be the same, unless a mixture of starting materials is used.

The $R_2$ and $R_3$ groups can be linear or branched. In an embodiment, the dialkoxyalkanoate has a symmetrical carbon distribution, i.e., the same number of carbon atoms, such as 2 to 10 carbon atoms, or 3 to 8 carbon atoms in both $R_2$ and $R_3$. In an embodiment, $R_2$ and $R_3$ are non-symmetric, for example, wherein one of $R_2$ and $R_3$ is a $C_2$ or $C_3$ alkyl group, and the other is a $C_4$ to $C_8$ group. In an embodiment, either or both $R_2$ and $R_3$ have 1 to 6 branching methyl, ethyl, or propyl groups, such as 2 to 5, or 3 to 4 branching methyl or ethyl or propyl groups. In an embodiment, either or both $R_2$ and $R_3$ have 1 to 5 units of unsaturation, such as 2 to 3 units of unsaturation. In an embodiment, either or both $R_2$ and $R_3$ have a cyclic group with 3 to 6 members, such as 4 to 5 members. In an embodiment, $R_2$ is one of the following groups: isopentyl, isobutyl, n-butyl, isoamyl, or ethyl. In an embodiment, $R_3$ is one of the following groups: isopentyl, isobutyl, n-butyl, isoamyl, or ethyl.

In an embodiment, $R_2$ and $R_3$ are provided by the same alcohol reactant. In an embodiment, $R_2$ and $R_3$ are provided by different alcohol reactants. In an embodiment, a fuel composition includes multiple different $C_5$ to $C_{30}$ compounds corresponding to formula (I) with different selections from $R_1$, $R_2$, or $R_3$.

FIG. 2 shows several compounds made and tested for various properties to determine the effect of structure of the properties of the compound. Compounds with comparable C:O ratios but contrasting degrees of branching provide insight into the effect of substituents on fuel properties. These tests and examples are described further in the Examples section herein.

Figure 3:
FIG. 3 shows properties of soy biodiesel and isopentyl 2-(isopentyloxy)propanoate.

FIG. 3 shows as a comparison, similar properties of soy biodiesel and isopentyl 2-(isopentyloxy)propanoate. The data herein indicates the dialkoxyalkanoate compounds have some superior properties compared to biodiesel. For example, cloud point is a metric for evaluating the cold flow-properties of diesel fuels, these values go down to less than −60° C., such as −65° C. to −95° C., or −70° to −80° C. for the dialkoxyalkanoates, which is a substantial improvement over conventional biodiesel, and similar to the isopentyl 2-(isopentyloxy)propanoate, an alkoxyalkanoate. In addition, as discussed above, this is in a bioderived fuel or performance additive that is only steps away from a renewable biomass feedstock, and also can be scaled up and synthesized on a continuous basis with environmentally friendly reagents, e.g., non-halogen/non-heavy metal-containing reagents.

These results demonstrate the potential for the dialkoxyalkanoate compounds to be used as neat fuels or in high blend volumes with diesel for use as all-weather fuels in autoignition engines, while also increasing engine performance and fuel economy as compared to traditional biodiesel. The dialkoxyalkanoates can also be used in gasoline blends or as neat or blended fuels for spark ignition engines.

In an embodiment, the dialkoxyalkanoate compound has a derived cetane number (DCN) of 10 to 75, such as, for example, 20 to 50, or 45 to 60. This is compared to the DCN of B100 Biodiesel (comprising FAME compounds) of 62.6 or soy biodiesel of 52.

In an embodiment, the dialkoxyalkanoate compound has a Cloud Point of less than −60° C. This is contrasted to the cloud point of B100 Biodiesel of about −1° C. and 0.5 for soy biodiesel.

In an embodiment, the dialkoxyalkanoate compound has an LHV of 25 to 40 MJ/kg, such as, for example, 27 to 38 MJ/kg, or 30 to 35 MJ/kg. This compares to the LHV of B100 Biodiesel and soy biodiesel of 37 MJ/kg.

In an embodiment, the dialkoxyalkanoate compound has a YSI (yield sooting index) of 200 to 400, such as, 210 to 350, or 220 to 330. This compares to the LHV of biodiesel of 500 to 1000 depending on the lipid feedstock. The YSI of a FAME soybean oil used as a standard commercial feedstock biodiesel is 550. In an embodiment, the dialkoxyalkanoate compound has a C:O ratio (molar) of 1.67 to 10.0, such as, for example, 2.67 to 7.0, or 4.33 to 6.0.

The examples disclosed herein indicate the compounds disclosed herein have improvements across multiple measured properties.

The examples herein are performed with neat examples of the dialkoxyalkanoate compounds; however, the results indicate that the dialkoxyalkanoate compounds are also of interest as blending agents in traditional fuels in internal combustion engines.

In an embodiment, a fuel blend comprises a portion of dialkoxyalkanoate and a portion of a fuel selected from the group consisting of: gasoline, alcohols (for example, ethanol, methanol, or butanol), diesel fuel, biodiesel, jet fuel, marine fuel, or combinations thereof.

In an embodiment, the dialkoxyalkanoate component comprises 51% to 99.9% of the total fuel by liquid volume, such as, for example, 60% to 98%, or 80% to 95%, and the minority portion of the fuel is a conventional fuel selected from those listed herein, for example, 5% to 0.01%, 20% to 5%, or 40% to 10% of the total fuel by liquid volume. In an embodiment, a majority portion dialkoxyalkanoate is present with a minority conventional fuel in a volume ratio of 99.9:0.1 to 51:49, 95:5 to 70:30, or 90:10 to 60:40.

In another embodiment, the majority conventional portion fuel comprises 51% to 99.9% of the total fuel by liquid volume, such as, for example, 60% to 98%, or 80% to 95%, and the minority portion of the fuel is the dialkoxyalkanoate, for example, 5% to 0.01%, 20% to 5%, or 40% to 10% of the total fuel by liquid volume. In an embodiment, the majority conventional portion fuel is present with the dialkoxyalkanoate component in a volume ratio 99.9:0.1 to 51:49, 95:5 to 70:30, or 90:10 to 60:40.

In an embodiment, low-cost, conventional fuels may have certain fuel properties modified with the dialkoxyalkanoate blending agent, so that the value is improved to a level that is advantageous in conventional commercial vehicles. In an embodiment, the dialkoxyalkanoate compounds may also be used as a blending agent in fuels with lower DCN, such as currently available pump diesel fuels to create a fuel with a DCN above current levels for biodiesel. From the trends shown in the examples section, it is hypothesized that the cloud point of the fuel blend can be lowered, for example, by 5 to 80° C., such as 10 to 60° C., or 15 to 30° C. lower than the cloud point of the conventional biodiesel fuel alone by adding an effective amount of the dialkoxyalkanoate blending agent.

The blending of the gasoline, diesel, or alcohol fuel and the dialkoxyalkanoate compound can be performed at the pump, for example, as a blending agent blended into the fuel in the underground containers at the filling station. In another example, two separate tanks at the filling station would be filled. One with majority portion fuel, e.g. gasoline or diesel, and one with the dialkoxyalkanoate compound, and they would come together and be mixed in the pump, as the vehicle is fueled. The blending agent can also be added directly to the gas tank of a vehicle that is separately filled with fuel. It could also be blended at the supplier just prior to shipment to the filling station. In any of these manners, the fuel blend could be changed depending on the climate/temperature of the season and filling location.

In an embodiment, the dialkoxyalkanoate compound demonstrates a degree of chemical stability. For example, at an acidic pH of 2 and a temperature of 40° C., the $^1$H NMR of Compound 1 shows no significant degradation of ketal or ester functionality, after 1 to 60 days, such as 2 to 30 days, or 3 to 7 days.

A method for powering an internal combustion engine includes combusting a fuel to drive a piston in a cylinder of the engine. The fuel comprises an dialkoxyalkanoate compound selected from: diesel, gasoline, alcohol fuel, biodiesel, jet fuel, marine fuel, Fischer-Tropsch fuel, or combinations thereof. In an embodiment, the dialkoxyalkanoate compound is all or a majority portion of the total fuel used in the engine, particularly in autoignition engines.

In an embodiment, the dialkoxyalkanoate compound is used in autoignition engines, such as diesel engines, MCCI, Homogeneous Charge Compression Ignition (HCCI) engines, or more generally in Low-Temperature Gasoline Combustion (LTGC) engines (using gasoline-like fuels), that have the high-efficiency advantages of HCCI but can operate with some level of charge inhomogeneities. The term LTGC includes HCCI and stratified, partially stratified, and spark-assisted variants that still provide the high efficiency and low emission of HCCI, but work better over a wider operating range. See, for example, Dec, J. E., Yang, Y., Ji, C., and Dernotte, J., "Effects of Gasoline Reactivity and Ethanol Content on Boosted, Premixed and Partially Stratified Low-Temperature Gasoline Combustion (LTGC)," SAE technical paper no. 2015-01-0813, accepted for publication in the SAE J. of Engines, 2015 incorporated herein by reference. These engines are unconventional in use, but are known in the art, and do not need further description in detail to those of ordinary skill in the art.

A section including working examples follows, but, as with the rest of the detailed description, should not be read to be limiting on the scope of the claims.

EXAMPLES

Unless otherwise noted, all reactions were carried out in oven-dried glassware sealed with rubber septa under argon atmosphere with Teflon-coated magnetic stir bars. All reagents were purchased from Sigma Aldrich or Alfa Aesar and were used without further purification unless otherwise stated. All reactions were monitored by TLC, GCMS or NMR analysis. $^1$H spectra were referenced to residual solvent (Chloroform-d: 7.26 ppm, $^1$H). Soy derived B100 was acquired from Louis Dreyfus (batch #20368) and used as received.

In Example 1, the following reactants and amounts were used. Product theoretical yield is provided.

TABLE 1

| Reactants | Formula Wt. | M (g) | Equivalents | Mol |
|---|---|---|---|---|
| Pyruvic acid | 88.06 | 40.00 | 1 | 0.45 |
| Isoamyl Alcohol | 88.15 | 400.4 | 10 | 4.54 |
| H$_2$SO$_4$ | 98 | 2.23 | 0.05 | 0.023 |
| Product | 316 | 143.54 | 1 | 0.454 |

The reaction according to reaction scheme (1) below was performed:

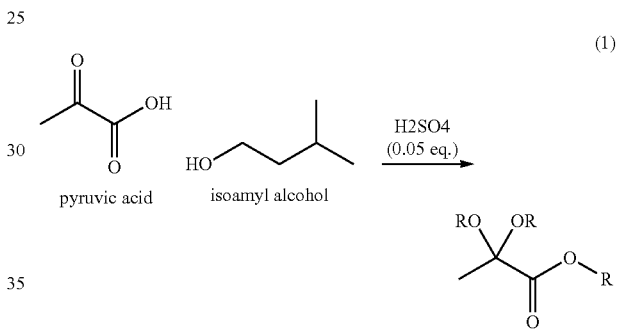

The reaction mixture was refluxed with a Dean Stark separator for 6 hours. This is an equilibrium-driven reaction that depends on water removal efficiency. Water was removed via the Dean-Stark apparatus by azeotropic layer separation.

The reaction mixture was directly washed with 4×400 mL H$_2$O, then washed with brine, dried and filtered.

The combined organic layers were concentrated in vacuo up to 70° C. at 7 mbar vacuum. Almost all isoamyl alcohol and diisoamyl ether side product were removed at this point.

200 g of crude product was received, which was about 75% yield. This was then distilled under high vacuum. A 120° C. thermal bath at 26 mT pressure provided a distillate at about 1 mL/min and 87° C. head temperature.

Examples 2-8 and Control Example

FIG. 2 shows 7 Examples of dialkoxyalkanoate compounds and one control example, acetaldehyde diisoamyl acetal, that were synthesized and tested for several properties, as disclosed herein. Examples 2, 3, 4, 7 and 8 were synthesized as in Example 1, with varying mass yield, as provided in FIG. 2. Example 8 was retried and a distillation yield of 63% was obtained.

The yields differed because the water azeotrope of shorter alcohols do not phase separate as well, meaning water is less efficiently removed from the reaction, providing lower conversion. A co-azeotrope such as hexane/toluene as mentioned above can address this issue. Glyoxylic acid was a much more reactive starting material for acetal formation than pyruvic acid. This is why its yield is quite high.

Examples 5 and 6 included a second step (b) as shown in FIG. 1 to conduct a base-catalyzed transesterification to selectively modify the $R_3$ group of the dialkoxyalkanoate. This was conducted in a similar manner as above with 50 eq of the ethyl or isoamyl alcohol, and 0.15 equivalents of KOH base.

Figure 4:
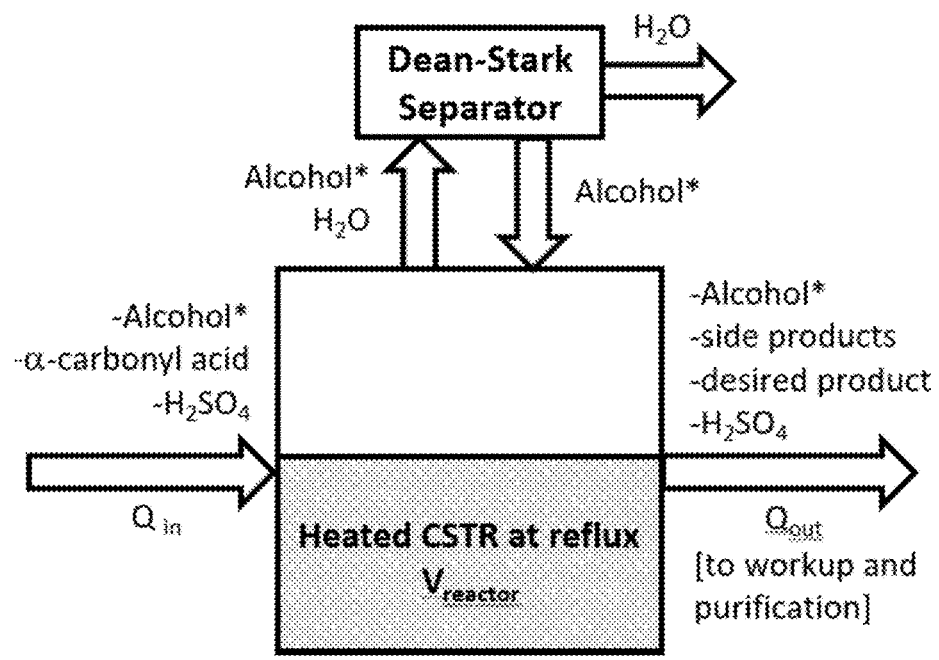
FIG. 4 is a diagram of the apparatus used for running the continuous reaction for Example 2.

Example 2 was also run a second time in a continuous manner, which resulted in a product with slightly different Fuel Properties as shown in FIG. 2. This was run in accordance with the diagram shown in FIG. 4. Here, a first reaction according to step (a) was run until sufficient conversion, such as, 70% or more, was achieved. A Dean-Stark separator was used to aid in water removal. This reaction product was then pumped out at a rate of 0.3 mL/min as new reactants were added at the same rate, thereby maintaining a steady-state volume of about 500 mL in the round bottom flask (RBF), which was a continuously stirred tank reactor (CSTR). The RBF was heated at 165° C. The continuous reaction was supplied with 2 L of reactant solution over 4 days. Overall, the theoretical yield was 791 g, crude yield was 690 g, and isolated yield from distillation was 251 g (32%).

Flow rate in an initial example was varied to find the best tradeoff between conversion and throughput, and it was about 0.3 mL/min. With a 0.3 mL flow rate and 500 mL volume, there was residence time ($t_{res}$) of 28 hours. Residence time is the average amount of time a reactant molecule spends in the reactor. It is calculated by: V_reactor/output flow rate. As shown on FIG. 4, $Q_{in}$ and $Q_{out}$ are in flow and out flow rates.

In a prophetic example, a PTFE membrane and third HPLC pump is used to automate the water separation process facilitated by the Dean-Stark trap.

The control Example was run at room temperature and with 10 eq isoamyl alcohol and 10 mol % Amberlyst 15 catalyst according to the following reaction Scheme 2.

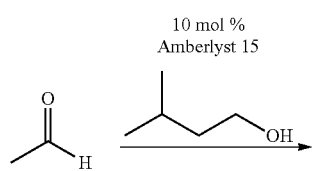

(2)

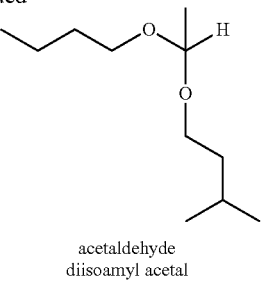

acetaldehyde
diisoamyl acetal

Example 2 was tested for stability under conditions of aqueous solution at a pH of 2 for 3.5 days at 40° C. After this period, no significant degradation of ester or ketal functionality was seen in $^1$H NMR analysis.

Comparative Examples

FIG. 3 shows two comparative examples soy biodiesel and isopentyl 2-(isopentyloxy) propanoate along with DCN, LHV, YSI, and Cloud point data for each.

Soy-derived B100 biodiesel fuel was acquired from Louis Dreyfus Agricultural Industries, LLC (batch #20368), and used as received with properties and composition detailed by Fioroni et al., Screening of potential biomass-derived streams as fuel blendstocks for mixing controlled compression ignition combustion. SAE International Journal of Advances and Current Practices in Mobility 2019, 1, (2019-01-0570), 1117-1138. The fatty acid profile is shown in Table 2.

TABLE 2

| Components of Soy-derived B100 Biodiesel Fuel | | | | | | | | | |
|---|---|---|---|---|---|---|---|---|---|
| Fatty Acids | Myristic | Palmitic | Palmitoleic | Stearic | Oleic | Linoleic | Linolenic | Arachidic | Other |
| $C_{total}$: Unsaturation | 14:00 | 16:00 | 16:01 | 18:00 | 18:01 | 18:02 | 18:03 | 20:00 | |
| Composition[a] (% w/w) | 0.07 | 10.84 | 0.27 | 4.52 | 23.21 | 52.73 | 7.34 | 0.41 | 0.61 |

[a]Normalized mass fractions are values based on GCMS analysis of the B100 blend.

As shown in FIGS. 2 and 3, both the alkoxyalkanoate isopentyl 2-(isopentyloxy)propanoate, and the several examples of dialkoxyalkanoates have a good balance of properties with improvements over conventional soy biodiesel. Soy biodiesel is a mixture of fatty acid methyl esters (FAME), which varies based on the soybean feedstock used. The five dominant FAME components in soy biodiesel are shown. Experimental values were measured based on a standard soy methyl ester sample described in the fuel property database at fuelsdb.nrel.gov. The synthetic method of dialkoxyalkanoate production is amenable to a continuous process, as disclosed herein and does not require use of halogenated reactants. They also may provide even lower cloud point properties than the comparative alkoxyalkanoate.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A method for making a fuel product for an internal combustion engine at least partially from a biomass source, the method comprising the steps of reacting a $C_1$ to $C_9$ alcohol and an alpha-carbonyl acid in a solvent to form a dialkoxyalkanoate; blending the dialkoxyalkanoate with a fuel to make a blended fuel, the fuel being selected from the group consisting of: gasoline, diesel, alcohol fuel, biodiesel, jet fuel, marine fuel, Fischer-Tropsch fuel, or combinations thereof; wherein the dialkoxyalkanoate is blended in a ratio of 99.9:5 to 51:49 by volume to the fuel and wherein the dialkoxyalkanoate is a $C_5$ to $C_{30}$ dialkoxyalkanoate.

2. The method of claim 1, further comprising adding an acid catalyst in the step of reacting the $C_1$ to $C_9$ alcohol and the alpha-carbonyl acid in the solvent to form the dialkoxyalkanoate.

3. The method of claim 1, wherein no halogenated compounds are used in the method.

4. The method of claim 1, wherein the dialkoxyalkanoate corresponds to formula (I):

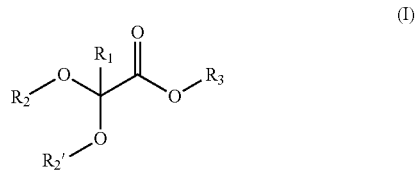

wherein the $R_1$ group is —H or a —$CH_3$ group, the $R_2$ and $R_2$' groups are alkyl groups independently selected to have 1 to 9 carbon atoms; and the $R_3$ group is selected to have 1 to 9 carbon atoms.

5. The method of claim 1, further comprising reacting the dialkoxyalkanoate with a different $C_1$ to $C_9$ alcohol in a base-catalyzed transesterification reaction.

6. The method of claim 1, further comprising performing the method in a continuous process.

7. The method of claim 1, further comprising the step of blending the dialkoxyalkanoate with a fuel to make a blended fuel, the fuel selected from the group consisting of: diesel, biodiesel, alcohol, or combinations thereof.

8. The method of claim 7, wherein the dialkoxyalkanoate is blended in a ratio of 99.9:5 to 51:49 by volume to the fuel.

9. The method of claim 1, further comprising adding an effective of amount of the dialkoxyalkanoate to lower a cloud point of the blended fuel 5 to 50° C. lower than the fuel alone.

10. The method of claim 7, further comprising adding an effective of amount of the dialkoxyalkanoate to lower a cloud point of the blended fuel 5 to 50° C. lower than the fuel alone.

11. The method of claim 1, wherein the fuel is blended in a ratio of 99.9:0.1 to 51:49 by volume to the dialkoxyalkanoate.

12. The method of claim 7, wherein the fuel is blended in a ratio of 99.9:0.1 to 51:49 by volume to the dialkoxyalkanoate.

13. The method of claim 1, wherein the alpha-carbonyl acid is pyruvic acid or glyoxylic acid.

14. The method of claim 1, wherein the $C_1$ to $C_9$ alcohol is produced from microbial fermentation of the biomass source.

15. The method of claim 14, wherein the $C_1$ to $C_9$ alcohol is a fusel alcohol.

16. The method of claim 1, wherein the dialkoxyalkanoate has a yield sooting index of 200 to 400.

17. The method of claim 1, wherein the $C_1$ to $C_9$ alcohol is branched.

18. The method of claim 1, wherein the fuel product is formulated for use in an autoignition engine.

* * * * *